United States Patent [19]

Larkin et al.

[11] 3,931,264
[45] Jan. 6, 1976

[54] METHOD FOR RECOVERING SOLUBILIZED ORGANOTIN HALIDES

[75] Inventors: William A. Larkin, Morristown; Jean W. Bouchoux, Nutley, both of N.J.

[73] Assignee: M & T Chemicals Inc., Greenwich, Conn.

[22] Filed: Aug. 22, 1974

[21] Appl. No.: 499,503

[52] U.S. Cl. ............................................. 260/429.7
[51] Int. Cl.² ........................................... C07F 7/22
[58] Field of Search ................................. 260/429.7

[56] References Cited
UNITED STATES PATENTS

| | | | |
|---|---|---|---|
| 2,569,492 | 10/1951 | Passino et al. | 260/429.7 |
| 3,297,732 | 1/1967 | Banks | 260/429.7 |
| 3,389,158 | 6/1968 | Kushlefsky | 260/429.7 |
| 3,404,167 | 10/1968 | Gray | 260/429.7 |
| 3,415,857 | 12/1968 | Hoye et al. | 260/429.7 |
| 3,519,665 | 7/1970 | Molt et al. | 260/429.7 |

OTHER PUBLICATIONS

Weissberger et al., Techniques of Organic Chemistry; III; 1950; Interscience, N.Y., N.Y., p. 402–410.

*Primary Examiner*—Arthur P. Demers
*Attorney, Agent, or Firm*—Robert P. Auber; Kenneth G. Wheeless; Robert Spector

[57] ABSTRACT

Certain organotin halides can be recovered in substantially quantitative yield from their aqueous solutions by adding a non-reactive highly soluble inorganic salt to partially or completely saturate the solution and then heating the resultant solution as required to effect a separation of the organotin halide from the aqueous phase.

6 Claims, No Drawings

METHOD FOR RECOVERING SOLUBILIZED ORGANOTIN HALIDES

BACKGROUND

This invention relates to a method for recovering certain water-soluble organotin halides from aqueous solutions containing the organotin compounds.

Organotin halides of the general formula $R_aSnX_{4-a}$ wherein each R represents a hydrocarbon radical, particularly a lower alkyl radical and X represents chlorine, bromine or iodine, and a is 1, 2 or 3 are employed as biocides for controlling a variety of undesirable organisms and as auxiliary heat stabilizers for halogen-containing polymers. A major portion of the organotin halides produced are employed as intermediates for preparing organotin derivatives that are useful as catalysts, herbicides, insecticides, anti-microbial agents and for a variety of other applications in the agricultural, coating and chemical industries. When applied to heated glassware such as bottles and other containers, organotin halides decompose to yield an adherent coating of stannic oxide on the glass. This is often the first step in forming conductive, protective or decorative coatings on glass containers.

During the preparation and use of organotin halides, these compounds are often present as a solution or emulsion in water. Since the organotin compounds are relatively costly and may exhibit significant mammalian toxicity, an attempt is usually made to recover substantially all of these compounds from their aqueous solutions. In addition it is often desirable to recover the halides in a relatively pure form. This is particularly true during the preparation of these compounds, at which time they are usually combined with other organotin compounds which must be absent from the final product. A conventional method for recovering water-soluble organotin halides from an aqueous solution is by distillation whereby a portion or all of the water is boiled off, leaving a residue of the desired organotin compound. If the organotin compound is present in combination with other water-soluble organotin compounds, the boiling points may differ sufficiently to permit separation of the organotin compounds by fractional distillation once the water is removed. Distillation may not be possible without significant loss of product if the boiling point of the organotin halide is close to that of water, if the organotin compound and water form an azeotropic mixture or if the organotin compound decomposes to any appreciable extent when heated to the temperature required to remove the water. Even if the desired separation can be effected by distillation, the process requires expensive equipment and considerable amounts of energy in the form of heat. In addition, the recovered organotin compound may require further processing to attain the desired level of purity. Organotin halides that melt above ambient temperature can often be purified by recrystallization, however this requires an additional process step and the use of organic solvents. Since many of the organic solvents are flammable and/or volatile, they present a hazard to the safety and health of personnel handling these materials in addition to increasing manufacturing costs.

An objective of this invention is to provide a simple, relatively low cost method for recovering some of the water-soluble organotin halides in relatively pure form and high yield from aqueous solutions containing these compounds. It has now been found that this objective can be achieved by adding to the aqueous solution containing certain organotin halides a strong inorganic electrolyte in an amount sufficient to form a partially or completely saturated solution at ambient temperature and then heating the resultant solution as necessary to effect separation of the organotin halide.

SUMMARY OF THE INVENTION

This invention provides a method for isolating a liquid or solid organotin halide of the formula $(CH_3)_aSnX_{4-a}$ or $C_4H_9SnX_3$ in substantially pure form from an aqueous solution containing more than about 2% by weight of said organotin halide, the method consisting essentially of the following sequence of steps:

1. combining with said aqueous solution an amount of a water-soluble inert inorganic salt sufficient to attain a concentration of from 50 g. of said salt per 100 cc. of water up to the concentration equivalent to a saturated solution of said salt;
2. maintaining the temperature of the solution at between ambient and the boiling point of the solution as required to effect a separation of the organotin halide from the aqueous phase;
3. isolating the organotin halide.

In the foregoing formula a is the integer 2 or 3 and X represents chlorine, bromine or iodine.

DETAILED DESCRIPTION OF THE INVENTION

The present method for separating water-soluble organotin halides from an aqueous solution resembles the technique known as "salting out", whereby a strong electrolyte is added to an aqueous solution containing a solubilized weak electrolyte for the purpose of precipitating the latter from the solution as an immiscible liquid or solid. Once the aqueous solution containing the organotin halide has been combined with the inorganic electrolyte separation of the organotin halide as an immiscible liquid or solid occurs at ambient or elevated temperatures depending upon the particular organotin halide. The halide is readily isolated by conventional methods, which include decantation and filtration. Since the solubility of the inorganic electrolyte usually increases as the temperature is raised, it is unlikely that any of the electrolyte will precipitate from the solution along with the organotin halide.

Using the present technique it is feasible to recover at least 65% of an organotin halide from an aqueous solution containing as little as 2% by weight of halides containing 4 carbon atoms. Halides containing 2 or 3 carbon atoms are more soluble, and the minimum concentration level required to effect recovery of most of the halide present may therefore be correspondingly higher. All of the present compounds can be isolated when present at a concentration greater than about 55% by weight. If a given solution is too dilute for an effective separation using the present method, some of the water should be removed by distillation, which is preferably conducted under reduced pressure to avoid or at least minimize heat-induced decomposition of the organotin compound.

Depending upon the solubility of the organotin halide in water, the minimum concentration of inorganic salt necessary to completely precipitate the organotin halide is between 50 and 130% or more of the amount theoretically equivalent to a saturated solution of the salt at ambient temperature. Some salts will form super-saturated solutions under certain conditions, which would account for a higher solubility than the theoretical maximum.

The present method for isolating organotin halides from an aqueous solution of inorganic salts differs from a conventional "salting out" of weak electrolytes in that once the organotin compound separates from a heated saturated solution it cannot be redissolved when the solution is cooled to ambient temperature. The precipitation of weak electrolytes from aqueous solution is usually a reversible reaction, in that once the second phase forms it can be redissolved by adjusting the concentration of strong electrolyte, the temperature of the aqueous phase or both to levels at which a single phase exists.

Organotin halides that can be isolated using the present technique include dimethyltin dichloride, trimethyltin chloride, butyltin trichloride and corresponding compounds wherein the chlorine atoms of these three chlorides are replaced by bromine or iodine.

Inorganic salts suitable for precipitating the present organotin halides do not react with the organotin halide and are soluble at ambient temperature to the extent of at least about 50 g. per 100 cc. of water. Of the salts which meet these two criteria, preferred ones include the chlorides, bromides and iodides of zinc, calcium and manganese.

Other suitable readily available inorganic salts include, but are not limited to,
ammonium bromate
ammonium iodide
barium bromide
barium iodide
calcium nitrate
ferric halides
lead acetate
lithium bromide
magnesium acetate
nickel halides
potassium acetate
potassium carbonate
potassium fluoride
potassium iodide
sodium iodide
strontium bromide
strontium iodide The concentration of salt necessary to completely precipitate the organotin halide will vary depending upon the solubility of the organotin halide. Salt concentrations greater than 50 g. per 100 cc. of water are usually required to recover more than about 50% of the organotin halide. For the more soluble halides, such as dimethyltin dichloride, a saturated or super-saturated solution of the salt, equivalent to at least 200 g. of salt per 100 cc. of water, may be required to recover more than about 90% of the organotin compound.

The inorganic salt should be anhydrous to minimize the amount of salt required to precipitate the organotin compound. Some hydrated salts such as ferric chloride hexahydrate contain nearly equal amounts of salt and water. These hydrated salts are therefore too inefficient for use in the present method due to the inordinately large amount required to attain the desired concentration of salt in the solution.

The following example demonstrates preferred embodiments of the present method and demonstrates that the method cannot be employed with organotin halides that are not within the scope of the invention as defined in the accompanying claims. All parts and percentages are by weight.

EXAMPLE 1

The solubility in water of various organotin chlorides and an organotin bromide containing between one and eight carbon atoms was investigated using 10 parts or 55 parts of the organotin halide for each 100 parts of water. The mixture was then heated to 100°C. to determine whether the solubility of the halide at 100°C. differed from the value at 21°C. The results are summarized in the following table. Soluble compounds are indicated by the letter "s", unsoluble compounds by the letter "i".

TABLE I

| COMPOUND | PARTS OF COMPOUND/ 100 PARTS WATER | SOLUBILITY AT 21°C. | AT 100°C. |
|---|---|---|---|
| $CH_3SnCl_3$ | 10 | s | s |
|  | 55 | s | s |
| $(CH_3)_2SnCl_2$ | 10 | s | s |
|  | 55 | s | s |
| $(CH_3)_3SnCl$ | 10 | s | s |
|  | 55 | s | s |
| $C_2H_5SnCl_3$ | 50 | s | s |
| $(C_2H_5)_2SnBr_2$ | 50 | i | i |
| $C_4H_9SnCl_3$ | 10 | s | s |
|  | 55 | s | s |
| $(C_6H_5)_2SnCl_2$ | 10 | i | i |
| $C_8H_{17}SnCl_3$ | 10 | i | i |
| $(C_4H_9)_2SnCl_2$ | 10 | i | i |

An attempt was made to precipitate those organotin halides which dissolved using aqueous solution of calcium chloride were employed at each of the three temperatures. The concentration of the various solutions were as follows:

| Solution No. | Temperature of Solution | Grams of $CaCl_2.2H_2O$ per 100 cc. of water |
|---|---|---|
| 1 | 21°C. | 79.62 |
| 2 | 21°C. | 99.53 |
| 3 | 21°C. | 129.39 |
| 4 | 70°C. | 151.44 |
| 5 | 70°C. | 189.30 |
| 6 | 70°C. | 246.10 |
| 7 | 100°C. | 169.9 |
| 8 | 100°C. | 212.4 |
| 9 | 100°C. | 276.1 |

A 2 cc. portion of each of the nine organotin halide solutions listed in Table I was added to an 8 cc. portion of each of the nine calcium chloride solutions, which were then heated to the temperature specified in the following Table 2 and maintained at that temperature for five minutes. The percent by weight of the organotin halide present in the solution appears immediately below the formula for the organotin compound. The type of second phase which formed, if any, is noted. The absence of any entry indicates that only one phase was present.

TABLE 2

| Temp. of Solution | CaCl₂ Soln. No. | ORGANOTIN HALIDE | | | | | | | | |
|---|---|---|---|---|---|---|---|---|---|---|
| | | (control) $CH_3SnCl_3$ | | $(CH_3)_2SnCl_2$ | | $(CH_3)_3SnCl$ | | (control) $C_2H_5SnCl_3$ | $C_4H_9SnCl_3$ | |
| °C. | | 10% | 55% | 10% | 55% | 10% | 55% | 50% | 10% | 55% |
| 21 | 1 | — | — | — | slight ppt. | slight ppt. | gel | — | slight ppt | — |
| 21 | 2 | — | — | — | heavy ppt. | slight ppt. | oil | — | slight ppt. | slight oil |
| 21 | 3 | — | — | — | heavy ppt. | ppt. | oil | — | slight oil | slight oil |
| 70 | 4 | — | — | — | heavy ppt. | — | oil | — | — | heavy oil |
| 70 | 5 | — | — | — | heavy ppt. | — | heavy oil | — | — | heavy oil |
| 70 | 6 | — | — | — | heavy ppt. | — | heavy oil | — | — | heavy oil |
| 100 | 7 | — | — | — | heavy ppt. | — | heavy oil | — | — | heavy oil |
| 100 | 8 | — | — | — | heavy ppt. | — | heavy oil | — | heavy oil | heavy oil |
| 100 | 9 | — | — | — | heavy ppt. | — | heavy oil | — | heavy oil | heavy oil |

Note:
ppt = solid precipitate

The data in Table 2 demonstrate that while methyltin trichloride and ethyltin trichloride are soluble in water, they cannot be recovered using the present method, which, for all practical purposes, is limited to organotin halides containing 2 or 3 methyl radicals or one butyl radical. Certain asymmetric organotin halides, such as methyl ethyltin dihalides and methyl propyltin dihalides may be recoverable from aqueous solutions using the present technique, however these compounds are either highly toxic or so difficult to prepare that they are of limited commercial interest.

What is claimed is:

1. A method for isolating an organotin halide of the general formula $(CH_3)_aSnX_{4-a}$ or $C_4H_9SnX_3$, wherein a is the integer 2 or 3 and X represents chlorine, bromine or iodine, in substantially pure form from an aqueous solution containing more than about 2% by weight of said organotin halide, the method consisting essentially of the following steps:
   1. combining said aqueous solution with an amount of a chemically inert water-soluble, inorganic salt sufficient to attain a concentration of from 50 g. to said salt per 100 cc. of water up to the concentration equivalent to a saturated or super-saturated solution of said salt;
   2. maintaining the temperature of the solution at between ambient and the boiling point of the solution as required to effect a separation of the organotin halide from the aqueous phase;
   3. isolating the organotin halide.

2. A method as described in claim 1 wherein X is chlorine.

3. A method as described in claim 1 wherein the water-soluble inorganic salt is a halide of calcium, zinc or manganese.

4. A method as described in claim 3 wherein the halide is a chloride. per cent.

5. A method as described in claim 4 wherein the chloride is calcium chloride. per cent.

6. A method as described in claim 1 wherein the concentration of said inorganic salt is equivalent to a saturated solution of said salt in the presence of the organotin halide.

* * * * *

UNITED STATES PATENT OFFICE
CERTIFICATE OF CORRECTION

Patent No. 3,931,__4          Dated January 6, 1976

Inventor(s) William A. Lar___ and J___ __. Bouchoux

It is certified that error appears in the above-identified patent and that said Letters Patent are hereby corrected as shown below:

Claim 4, line 2 - Delete the word "per cent".

Claim 5, line 2 - Delete the word "per cent".

Signed and Sealed this

*twenty-third* Day of *March 1976*

[SEAL]

Attest:

RUTH C. MASON
*Attesting Officer*

C. MARSHALL DANN
*Commissioner of Patents and Trademarks*